United States Patent [19]

Morris et al.

[11] Patent Number: 5,586,970
[45] Date of Patent: Dec. 24, 1996

[54] ARTICULATING ADJUSTABE CONDYLAR PAD FOR KNEE BRACE

[75] Inventors: John Morris, Castro Valley; Gary Stafford, Hayward, both of Calif.

[73] Assignee: Orthopedic Technology, Inc., Tracy, Calif.

[21] Appl. No.: 379,313

[22] Filed: Jan. 23, 1995

[51] Int. Cl.$^6$ ........................................................ A61F 5/00
[52] U.S. Cl. .................................................. 602/26; 602/16
[58] Field of Search .............................. 602/5, 6, 16, 23, 602/26; 128/845, 846, 869, 882

[56] References Cited

U.S. PATENT DOCUMENTS

| | | | |
|---|---|---|---|
| 4,940,045 | 7/1990 | Cromarti | 602/26 X |
| 4,991,571 | 2/1991 | Kausek | 602/26 X |
| 5,022,391 | 6/1991 | Weidenburner et al. | 602/26 X |
| 5,259,832 | 11/1993 | Townsend et al. | 602/26 X |
| 5,376,134 | 12/1994 | Biedermann | 602/26 X |

*Primary Examiner*—Linda C. Dvorak
*Attorney, Agent, or Firm*—Townsend and Townsend and Crew

[57] ABSTRACT

An activity knee brace is disclosed in which the structural hinge axis of the brace moves to overlie the changing center of pivot of the condyle of the femur with respect to the plateau of the fibula-tibia. The brace consists of a thigh portion, a lower leg portion, and a structural hinge axis therebetween. The thigh portion supports the brace in the thigh; the lower leg portion supports the brace to the lower leg. The thigh portion is braced at the lower end at the medial supracondylar area by lateral and medial condylar pads in conjunction with an adjustable strap system. Provision is made to differentially adjust the lateral and medial condylar pads towards one another over the supracondylar hollow to affix and track the relative movement of the supracondylar hollow of the femur relative to the plateau of the fibula tibia. A pivot for the lateral and medial condylar pads is provided off axis with respect to the structural hinge of the brace. This pivot mates with a lineal cam on the pad, allowing towards and away movement of the condylar pads from the structural pivot of the brace. The towards and away movement of the condylar pads is in turn limited by arcuate cam which acts at approximate right angles to the lineal cam. Accordingly, dependent upon the angle of the condylar pads with respect to the thigh brace, dynamic adjustment of the structural hinge axis to overly the center of pivot of the knee occurs.

5 Claims, 3 Drawing Sheets

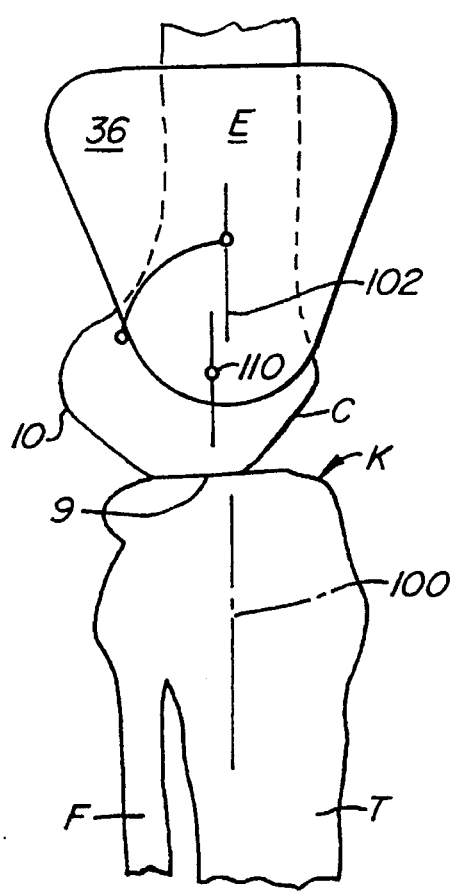
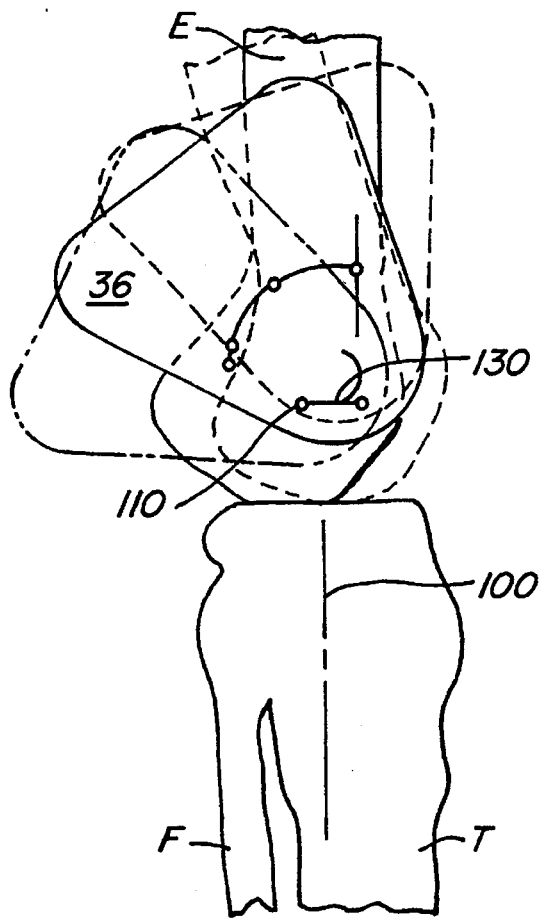
FIG. 6.
FIG. 7.
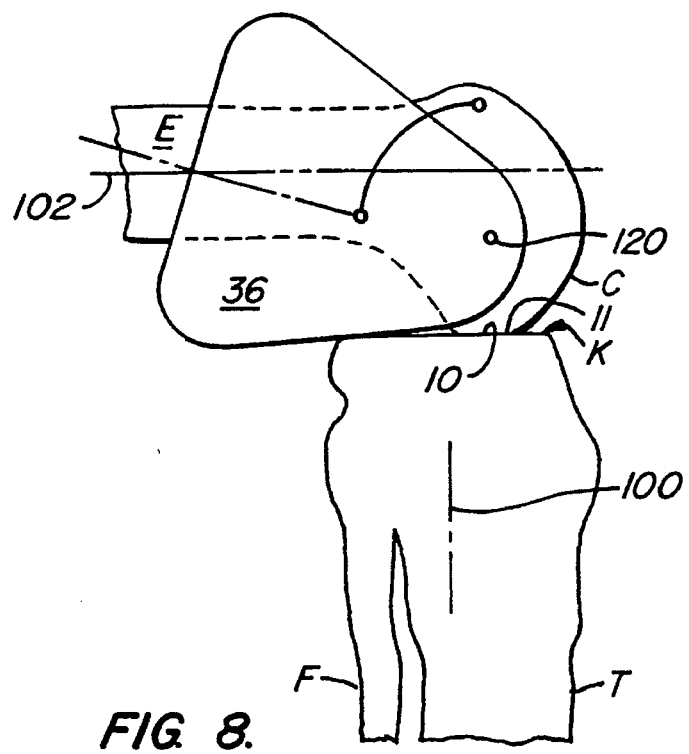
FIG. 8.

ARTICULATING ADJUSTABE CONDYLAR PAD FOR KNEE BRACE

This invention relates to knee braces. More particularly, the disclosed knee brace is an activity type brace useful for reinforcing the knee during activity or alternatively useful with a lower leg prothesis to support the prothesis and keep it properly positioned during use.

BACKGROUND OF THE INVENTION

Knee braces are known. They typically include a thigh member for fastening to the thigh, a lower leg member for fastening to the lower leg and a hinge axis therebetween positioned over the knee to be reinforced. All manner of straps for securing the respective leg and thigh portions have been illustrated in the prior art.

1. Brief Description of the Relevant Art

The following prior art includes a representative sample of such prior art.

Some knee braces have included compound hinges. Such compound hinges include two or more pivot points closely spaced along the natural joint defined by the knee. Examples of such compound hinges include Lerman U.S. Pat. No. 4,372,298; Marquette U.S. Pat. No. 4,793,333; Kausek et al. 4,732,143; and European Patent Application 0173161 to Townsend.

A knee stabilizer is disclosed in Marquette U.S. Pat. No. 4,790,299 having a supracondylar support. This supracondylar support provides vertical location of the brace on the leg at the supracondylar hollow.

Many braces rely on a simple hinge axis rigidly braced with respect to the knee. Example of such devices include Ford U.S. Pat. No. 4,624,247; Martin et al. U.S. Pat. No. 4,503,846 and Myers et al. U.S. Pat. No. 4,802,466.

There is a known tendency of some knee braces to "piston" with respect to the leg. Such piston movement can be accommodated by various springs between the respective knee brace portions. Illustrative of such a spring arrangement is Carsalade British Patent Application 2,156,221.

2. Statement of the Problem

The knee, unlike the common hinge, has an asymmetrical hinging action. As the knee bends, the pivot point about which the bending occurs, changes. Reference to the views provided by FIGS. 6, 7, and 8 of this application can illustrate this point.

In FIGS. 6–8 a typical knee joint is illustrated in rotation. The outlines of femur E, tibia T and fibula F are illustrated within a normal leg having conventionally proportioned tissue. The knee is shown in rotation from an extended disposition as shown in FIG. 6 to a position approximately maximum flexion as shown in FIG. 8. Intermediate rotational positions are shown in FIG. 7.

Some reference to the skeletal anatomy of the knee is beneficial. The lower leg includes a fibula F and the tibia T. These bones have their upper surface jointly defining plateau K upon which the corresponding condyle of the femur turns. Applicable cartilage, ligaments, and muscle are, of course, omitted.

For reference in the following discussion, the tibia has been provided with center line 100. The reader will understand that as this discussion proceeds that the center of rotation of the condyle of the femur changes with respect to the center line during movement of the knee between the extended and flexed positions.

The femur E includes condyle C. Condyle C is not symmetrical with respect to the femur. This can be seen by inspecting FIGS. 6–8. As in the case of the tibia, the femur E has been given center line 102. This center line will also be used to discuss the asymmetry of the knee joint requiring the improvement of this invention.

Femur E normally rests upon the plateau K of the tibia at surface 9. However, upon flexion, resting occurs on surface 11 at plateau K. It is apparent at first glance that the illustrated "hinge action" of the knee is not symmetrical. This phenomenon can be further understood by referring to the respective "centers of rotation" of the condyle of the femur overlying the lower leg.

When the knee first begins to rotate from a position of extension to a position of flexion, turning of the joint of the knee first occurs about center 110. It can be seen that this center 110 is to the left of the center line 100 of the fibula tibia and also to the left of the center line 102 of the femur E.

When the knee finishes rotation to a point of near maximum flexion illustrated in FIG. 8, final turning occurs about center 120. It can be seen that this center in FIG. 7 has moved to the right of center line 100 of the fibula tibia.

Referring to FIG. 7, an attempt to trace the migration of the center of pivot with respect to the condyle K and the tibia is instructive. Specifically, the center of pivot moves along line 130 as the leg moves from extension deflection. This begins with the extension center of pivot 110 on the left and ends with the flexion center of pivot 120 on the right.

Once this diagram is seen and understood, the futility of providing a knee with a simple hinge for reinforcement of the knee can be clearly understood.

Assume that the full dynamic load is placed on the knee joint and the brace together during active body movement. As set forth in the prior art, assume that the brace holds a hinge axis as rigidly as possible at one rigid hinge axis location with respect to the knee joint. However, the knee, undergoing both flexion and extension will have its center of pivot moved with respect to the rigid hinge axis. As all those familiar with the simple concept of mechanics know, something relative to the knee with its moving center of pivot, the brace (or both) has to give in order to permit hinging axis. Indeed, a recitation of undesirable knee brace motions can catalog such conforming movements of the knee relative to a brace to permit the required hinge like movement of the knee joint.

Where the hinge axis of the brace is rigidly held with respect to the knee joint, a phenomenon commonly known a "pistoning" frequently occurs. Either the thigh portion or the lower leg portion (or both) move up and down with respect to the thigh or lower leg. Absent such movement, bending of the knee could not occur. Skin abrasions and flesh irritations are a common result of such "pistoning" movement.

This dynamic misalignment between the rigid hinge axis of a knee brace and the moving center of pivot of a knee also causes discomfort to the reinforced knee joint itself. As those familiar with mechanics know, two closely positioned but misaligned hinge axes acting on the same levers (the thigh and the lower leg) work against each other with considerable force. This considerable force can cause discomfort at the knee joint and even damage to the reinforced knee over a period of time.

Clearly there is a need to emulate in a knee brace, especially an activity knee brace, movement to the braced hinge axis which correspond in large measure to the movement of the knee center of rotation.

Daneman et al. U.S. Pat. No. 5,078,127 issued Jan. 7, 1992 entitled Knee Brace with Articulating Brace Hinge Axis constituted an attempt to approximate the movement of an activity brace with the dynamics of the human knee. In that disclosure, the combination of a offset condylar pad was combined with a knee brace to approximate the movement of the structural hinge axis to overlying the dynamically moving center of rotation of a knee joint during flexure and extension. What follows is a further attempt to obtain tracking between the dynamically changing center of pivot of a knee joint and the structural hinge member of an activity brace.

SUMMARY OF THE INVENTION

An activity knee brace is disclosed in which the structural hinge axis of the brace moves to overlie the changing center of pivot of the condyle of the femur with respect to the plateau of the fibula-tibia. The brace consists of a thigh portion, a lower leg portion, and a structural hinge axis therebetween. The thigh portion supports the brace in the thigh; the lower leg portion supports the brace to the lower leg. The thigh portion is 10 braced at the lower end at the medial supracondylar area by lateral and medial condylar pads in conjunction with an adjustable strap system. Provision is made to compressively and differentially adjust the lateral and medial condylar pads towards one another over the supracondylar hollow and supracondylar depression. This serves the dual function of enabling the brace to optimally apply force at the joint line and to affix and track the relative movement of the supracondylar hollow of the femur relative to the plateau of the fibula tibia.

Regarding the tracking of the relative movement of the supracondylar hollow of the femur with respect to the plateau of the fibula tibia, a pivot for the lateral and medial condylar pads is provided off axis with respect to the structural hinge of the brace. This pivot mates with a lineal cam on the pad, allowing towards and away movement of the condylar pads from the structural pivot of the brace. The towards and away movement of the condylar pads is in turn limited by arcuate cam which acts at approximate right angles to the lineal cam. Accordingly, dependent upon the angle of the condylar pads with respect to the thigh brace, dynamic adjustment of the structural hinge axis to overlie the center of pivot of the knee occurs.

BRIEF DESCRIPTION OF THE DRAWINGS

FIG. 6 is a skeletal diagram of the knee illustrating the extended position of the knee;

FIG. 7 is a skeletal diagram of the knee intermediately bent between full flexion and full extension; and, FIG. 8 is a skeletal diagram of the knee at or near full flexion.

DESCRIPTION OF THE PREFERRED EMBODIMENT

Figure 1:
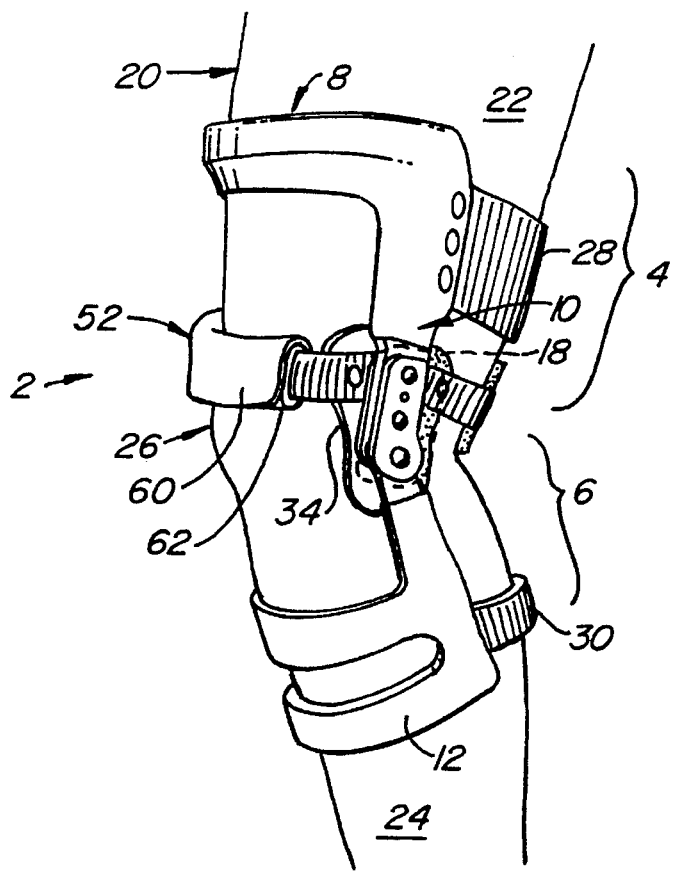
FIG. 1 is a perspective view of a knee brace incorporating the invention herein shown mounted to a user's leg.

FIG. 1 illustrates knee brace 2 made according to this invention. Knee brace 2 includes upper thigh brace portion 4 and lower leg portion 6. Upper thigh brace portion 4 includes curved upper part 8 and paired upper struts 10. Similarly, lower leg portion 6 includes curved lower part 12 and paired lower struts 14, it being understood that only the medial struts are illustrated in FIG. 1; the lateral struts are hidden from view. Corresponding upper and lower struts 10, 14 are pivotally mounted to one another by knee brace pivot assemblies 16. Each knee brace pivot assemblies 16 is covered by protective cover 18. The reader will understand that this protective cover 18 is shown only in FIG. 1; the protective cover is removed in all other views of this application.

Knee brace 2 is mounted to user's leg 20 with upper thigh brace portion 4 secured to the user's upper leg 22 and with lower leg portion 6 secured to user's lower leg 24, that is above and below user's knee 26. Upper strap 28 and lower strap 30 are fitted to respective paired upper struts 10 and paired lower struts 14 and fit against the back of user's leg 20.

Figure 2:
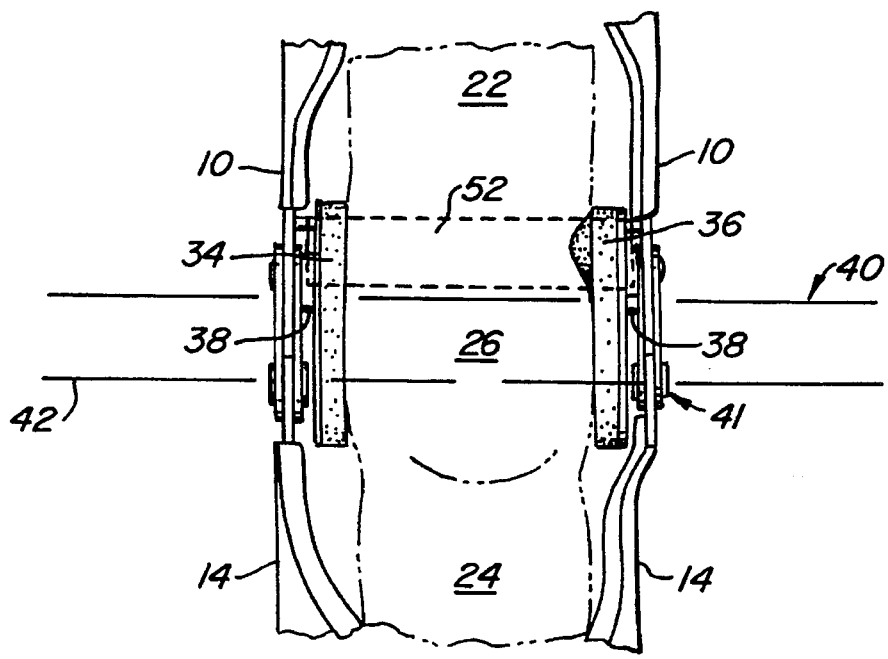
FIG. 2 is a front view of a user's knee showing portions of the brace forcing the condylar pads in intimate contact with the supracondylar hollows to firmly trace movement of the supracondylar hollow with respect to the lower leg.

Referring to FIG. 2, knee brace 2 further includes medial condylar pad 34 and lateral condylar pad 36. Medial condylar pad 34 is pivotally mounted to one of paired upper struts 10 by pivot pin 38 so as to pivot about horizontal pad axis 40. Likewise, lateral condylar pad 36 is pivotally mounted to one of paired upper struts 10 by pivot pin 38 so as to pivot about the same horizontal pad axis 40.

Knee brace 2 has main structural hinge 41. Main structural hinge 41 connects paired upper struts 10 and paired lower struts 14. This connection occurs at hinge axis 42. As will hereafter be emphasized, main structural hinge 41 is the principal load bearing member of knee brace 2. Further, main structural hinge 41 is given sufficient strength to accommodate differential loading exerted by medial condylar pad 34 and lateral condylar pad 36 when brace adjustment occurs.

As set forth in Daneman U.S. Pat. No. 5,078,127 issued Jan. 3, 1992 (now U.S. Pat. No. Re. 34,818 issued Jan. 3, 1995) entitled Knee Brace With Articulating Brace Hinge Axis it is preferred to offset pivot pins 38 with respect to hinge axis 42. Dependent upon the size of the individual utilizing the brace, such offset can vary from ⅞" to 1⅜".

It will be understood that medial condylar pad 34 and lateral condylar pad 36 have condylar strap 52 in combination with pad 60 held by hook and pile fasteners 62. The function of condylar strap 52 is to exert a uniform force strapping force across the tops of medial condylar pad 34 and lateral condylar pad 36. As previously disclosed in Daneman et al. U.S. Pat. No. 5,078,127, this strap has the function of bracing user's upper leg 22 to avoid so-call pistoning movement of the leg with respect to upper thigh brace portion 4 of knee brace 2.

Returning to FIG. 1, it will be seen that user's knee 26 is free for some movement with respect to paired upper struts 10. It is this freedom of movement urged by medial condylar pad 34 and lateral condylar pad 36 that constitutes the novelty of this disclosure. For the purposes of this disclosure, two types of movement are required.

First, it will be shown that each of medial condylar pad 34 and lateral condylar pad 36 is independently adjustable in side-to-side motion with respect to paired upper struts 10. This independent adjustment permits either medial condylar pad 34 or lateral condylar pad 36 to have variable pressure with respect to user's knee 26. In particular, a three point force/support system for the knee at the condylar pad is provided utilizing the brace.

Second, a further adjustment of the effective offset of pivot pin 38 with respect to main structural hinge 41 at hinge axis 42 is provided. Specifically, by applying to each condylar pad a system of cams, with an independent cam follower and pivot pin 38 being the other cam follower, dynamic adjustment of the respective condylar pads can occur to further approximate the dynamically changing center of pivot of the knee to hinge axis 42 of main structural hinge 41.

Figure 3:
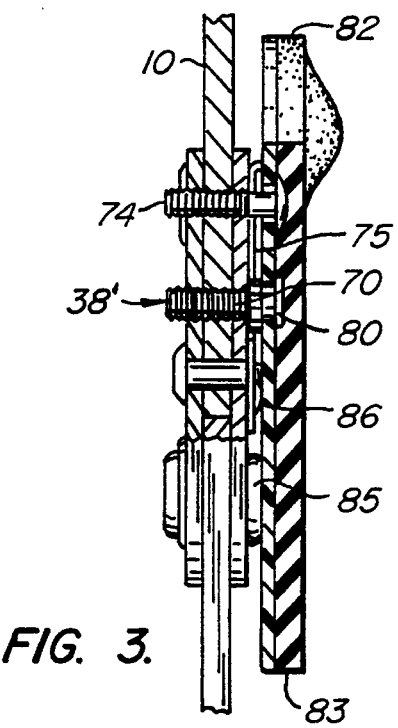
FIG. 3 is a side elevation of a preferred embodiment illustrating adjustment of a spring steel backing to the condylar pad to cause the pad to move inwardly and over the condyle of the femur.

Regarding the independent adjustment of either medial condylar pad 34 or lateral condylar pad 36, FIG. 3 provides an exemplary detail that can be utilized on either pad 34, 36. This can be best understood by explaining the theory relating to the operation of the pad followed by the implementation of the operation of the pad.

Where an individual has a compromised joint, the respective condylar pads 34, 36 can be utilized to apply differential pressure to the joint line. Specifically, it has been found that dependent on the particularities of the compromised joint, greater or lesser pressure at either medial condylar pad 34 or lateral condylar pad 36 is desired. Accordingly, independent adjustment of the respective pads along horizontal pad axis 40 can produce this differential pressure. Specifically, it will be remembered that upper thigh brace portion 4 and lower leg portion 6 of knee brace 2 are effectively fixed to user's leg 20. At the same time, main structural hinge 41 provides a more-or-less rigid connection between the respective upper thigh brace portion 4 and lower leg portion 6. Thus, where the respective medial condylar pad 34 and lateral condylar pad 36 are independently biased with respect to paired upper struts 10, this differential pressure can be generated.

Further, this is an activity brace. This being the case, it is desired to have dynamic loading of the brace be accompanied by the differential pressure of the respective condylar pads. This is realized by the independent adjustments set forth in FIGS. 3 and 5 which will be respectively discussed.

Referring to FIG. 3, pivot 38' includes screw 70 free to rotate at 80 and threaded into strut 10 so as to be laterally adjustable relative to upper strut 10. These respective set screw 70 enable pivot 38' to be adjusted relative to upper strut 10 Thus, at least at pivot 38', differential adjustment of lateral condylar pad 36 is provided. It will be understood that differential adjustment of medial condylar pad 34 is provided by an equivalent adjustment of its respective pivot 38'.

It is desirable to have condylar pads 34, 36 provided with an additional point of differential adjustment towards and away from user's knee 26. Accordingly, second set screw 74 in second threaded bushing 76 is provided. As will hereafter be more fully set forth, this respective second set screw 74 ends in cam follower 80 on the back of lateral condylar pad 36. Thus it has relative motion with respect to lateral condylar pad 36 permitting both the desired differential bias of the pad as well as the ability of the pad to pivot about pivot 38'.

It is desired that the respective condylar pads 34, 36 be backed by spring steel member 75 fastened at 140 of pivot assembly. Spring steel member 75 fastens at rivet 86 to upper strut 10. Screw 74 biases spring member 75 away from strut 10 and toward user's knee 26. This spring imparts extra flexibility against the condyle at the same time assuring a firm grip. Thus, the respective condylar pads are deformable over condyle C of user's knee 26. Further, it will be observed that second set screw 74 is below top 82 of lateral condylar pad 36. This being the case, it will be understood that second set screw 74 is leveraged in bias top 82 of lateral condylar pad 36 over condyle C of user's knee 26. We prefer that second set screw 74 and its cam follower 80 be above pivot 38'.

It will be observed that lower portion 83 of lateral condylar pad 36 rests against protruding pin 85 of main structural hinge 41 as well as rivet 86. Again, the back of lateral condylar pad 36 will move relative to these respective members so that the differential adjustment of set screw 70 and second set screw 74 will be produced on the condylar pads 34, 36 relative to these members.

Figure 5:
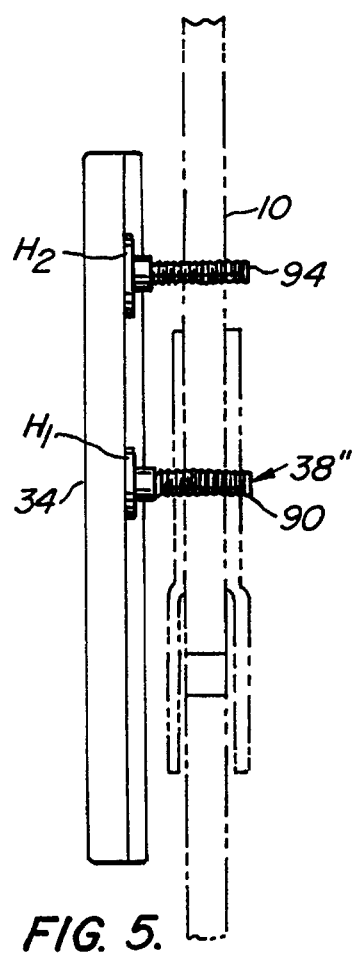
FIG. 5 is an alternate side elevation of an embodiment illustrating adjustment of the condylar pads.

Referring to FIG. 5, an alternate and less preferred embodiment is illustrated. Specifically, medial condylar pad 34 is shown supported from upper strut 10 by pivot 38". Pivot 38" is comprised of set screw 90, preferably of the Allen variety and includes cam follower head $H_1$ for fitting into a respective cam slot 92 on the back of medial condylar pad 34. Likewise, second set screw 94 has second cam follower head $H_2$ for fitting into second cam slot 96. It will be appreciated that unlike the embodiment of FIG. 3, the embodiment of FIG. 5 only includes two point support of medial condylar pad 34.

Having set forth the independently biased adjustment of medial condylar pad 34 and lateral condylar pad 36, the support of these respective pads on paired cams and cam followers can now be set forth.

Emphasis has been placed on the need to have main structural hinge 41 at its hinge axis 42 track the center of pivot of user's knee 26 as it moves along line 130 during movement from extension to flexion (See FIGS. 6–8). This need being present, and with reference to FIG. 4, a further way of approximating the desired movement is illustrated.

It will be seen that pivot 38" and its cam follower head $H_1$ fits in vertical cam slot 92. Vertical cam slot 92 is constructed in such a manner so that cam follower head $H_1$ is captured within the slot. It will thus be appreciated that medial condylar pad 34 is free to move vertically with respect to pivot 38".

Likewise, it will be seen that second set screw 94 has second cam follower head $H_2$ captured within second cam slot 96. This slot has two functions.

First, it permits medial condylar pad 34 to pivot relative to pivot 38". Second, and because second cam slot 96 is at an angle with respect to vertical cam slot 92, the center of pivot of medial condylar pad 34 relative to pivot 38" is changed. Simply stated, by tailoring respective cam slot 92 and second cam slot 96, further dynamic adjustability of the pivot of medial condylar pad 34 and lateral condylar pad 36 relative to hinge axis 42 of main structural hinge 41 is attained.

Figure 4:
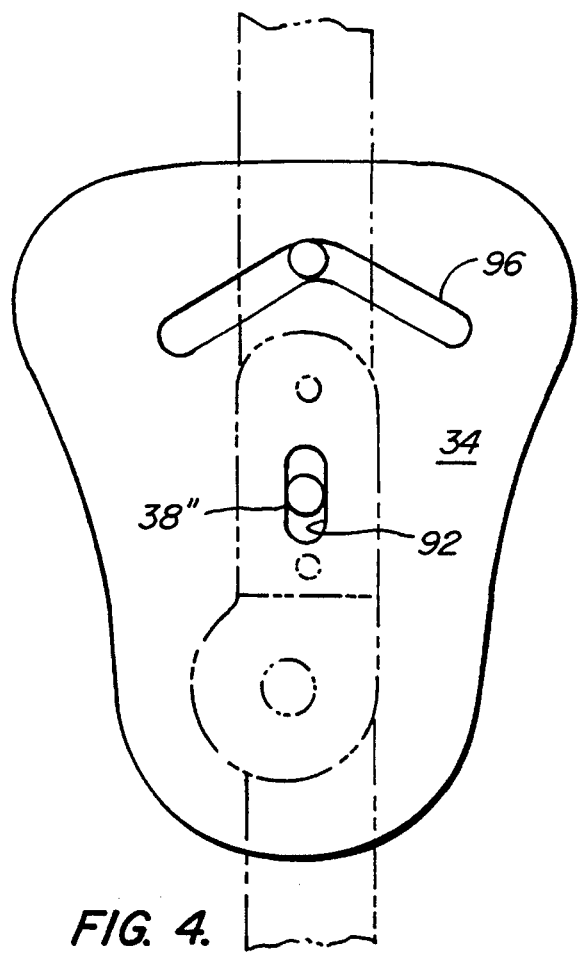
FIG. 4 is a plan view taken at the condylar pads illustrating the brace affixed pivot, the slotted attachment of the pivot to condylar pad, and the cam restricting condylar pad offset to enable the structural hinge of the brace dynamically track the moving center of pivot of the knee.

It will be understood that in this specification—especially with respect to FIGS. 3–5, we have treated medial condylar pad 34 and lateral condylar pad 36 identically. That is to say the illustrated mechanism that supports one condylar pad can be used for the support of the other pad. This has been done to avoid needless repetition.

It further will be understood that an activity knee brace is disclosed which can by adjusted to fit a wide range of individual knees having differing individual structure. It is further understood that a combination of adjustments of FIGS. 3 and 5 is possible and that the adjustments shown in FIGS. 3 and 5 are only two of the possible adjustments. Other ways of forcibly adjusting condylar pad 34, 36 relative to the support members will suffice.

What is claimed is:

1. An improved knee brace comprising:

a thigh brace portion mountable to the user's upper leg, the thigh brace portion including medial and lateral struts, said struts extending rigidly from said thigh brace portion downward to and through a hinge axis;

a lower leg portion, said lower leg portion including medial and lateral struts extending upwardly from said lower leg portion to and towards a hinge axis on either side of said leg;

a simple hinge mounted between said upper and lower struts on both sides of said knee brace, said simple hinge enabling pivot of said thigh brace portion relative to said lower leg portion along a first substantially horizontal hinge axis between positions of extension and flexion when mounted to the knee of a wearer;

medial and lateral condylar pads pivotally secured to the thigh brace portion of pivotal movement generally along a second substantially horizontal medial and lateral pivot pad axis, parallel to but offset from said first substantially horizontal hinge axis of said simple hinge, said second substantially horizontal medial and lateral pivotal pad axis spaced apart from the above first substantially horizontal axis of said hinge of said brace by a distance approximating articulation of said simple hinge axis from said thigh brace portion to follow the changing center of pivot of said knee during extension and flexion of said knee;

each said medial and lateral condylar pads including a first cam slot at said pivot for enabling said pad to move on said pivot towards and away from said pivot; and, each said medial and lateral condylar pads further including a second cam slot between said thigh brace portion and said pad for constraining said medial and lateral condylar pads to move on said pivot towards and away from said pivot to further approximate articulation of said simple hinge axis from said thigh brace portion to follow the changing center of pivot of said knee during extension and flexion of said knee.

2. An improved knee brace according to claim 1 and comprising in further combination:

each said medial and lateral condylar pads including a first adjustment at said pivot relative to a strut on said thigh brace for causing said medial and lateral condylar pads to move towards and away from said struts; and, each said medial and later condylar pad further including a second adjustment offset from said pivot relative to a strut on said thigh brace portion for causing said medial and lateral condylar pads to move towards and away from said struts whereby said first and second adjustments cause can adjustably accommodate the capture of the condyle of the femur.

3. An improved knee brace according to claim 1 and comprising in further combination:

said medial and lateral condylar pads inwardly deflected toward the femur above the femur condyle for capture to the respective medial supracondylar hollow and lateral supracondylar depression to restrain brace downward movement above the knee joint at a point superior to the center of pivot of condyle of the femur over the plateau of the tibia; and, strap means passed around said medial and lateral condylar pads to exert when tightened on said medial and lateral condylar pads to produce a snug fit with said medial and lateral supracondylar hollow to restrain pistoning movement of said thigh brace portion towards the joint of the user's knee.

4. An improved knee brace comprising:

a thigh brace portion mountable to the user's upper leg, the thigh brace portion including medial and lateral struts, said struts extending rigidly from said thigh brace portion downward to and through a hinge axis;

a lower leg portion, said lower leg portion including medial and lateral struts extending upwardly from said lower leg portion to and towards a hinge axis on either side of said leg;

a simple hinge mounted between said upper and lower struts on both sides of said knee brace, said simple hinge enabling pivot of said thigh brace portion relative to said lower leg portion along a first substantially horizontal hinge axis between positions of extension and flexion when mounted to the knee of a wearer;

medial and lateral condylar pads pivotally secured to the thigh brace portion of pivotal movement generally along a second substantially horizontal medial and lateral pivot pad axis, parallel to but offset from said first substantially horizontal hinge axis of said simple hinge, said second substantially horizontal medial and lateral pivotal pad axis spaced apart from the above first substantially horizontal axis of said hinge of said brace by a distance approximating articulation of said simple hinge axis from said thigh brace portion to follow the changing center of pivot of said knee during extension and flexion of said knee;

each said medial and lateral condylar pads including a first adjustment at said pivot relative to a strut on said thigh brace for causing said medial and lateral condylar pads to move towards and away from said struts; and, each said medial and later condylar pad further including a second adjustment offset from said pivot relative to a strut on said thigh brace portion for causing said medial and lateral condylar pads to move towards and away from said struts whereby said first and second adjustments cause can adjustably and differentially accommodate the capture of the condyle of the femur.

5. An improved knee brace according to claim 4 and comprising in further combination:

each said medial and lateral condylar pads including a first cam slot at said pivot for enabling said pad to move on said pivot towards and away from said pivot; and, each said medial and lateral condylar pads further including a second cam slot between said thigh brace portion and said pad for constraining said medial and lateral condylar pads to move on said pivot towards and away from said pivot to further approximate articulation of said simple hinge axis from said thigh brace portion to follow the changing center of pivot of said knee during extension and flexion of said knee.

* * * * *